United States Patent
Mori

(10) Patent No.: US 8,920,310 B2
(45) Date of Patent: Dec. 30, 2014

(54) IN-VIVO IMAGE DISPLAY APPARATUS AND RECEIVING SYSTEM

(75) Inventor: Takeshi Mori, Tokyo (JP)

(73) Assignees: Olympus Corporation, Tokyo (JP); Olympus Medical Systems Corp., Tokyo (JP)

( * ) Notice: Subject to any disclaimer, the term of this patent is extended or adjusted under 35 U.S.C. 154(b) by 1252 days.

(21) Appl. No.: 12/146,222

(22) Filed: Jun. 25, 2008

(65) Prior Publication Data

US 2008/0262298 A1 Oct. 23, 2008

Related U.S. Application Data

(63) Continuation of application No. PCT/JP2006/325529, filed on Dec. 21, 2006.

(30) Foreign Application Priority Data

Dec. 26, 2005 (JP) .................................. 2005-372670

(51) Int. Cl.
| | |
|---|---|
| A61B 1/04 | (2006.01) |
| A61B 5/07 | (2006.01) |
| A61B 1/00 | (2006.01) |
| A61B 5/00 | (2006.01) |

(52) U.S. Cl.
CPC ............. *A61B 5/073* (2013.01); *A61B 1/00009* (2013.01); *A61B 1/00016* (2013.01); *A61B 1/0005* (2013.01); *A61B 1/00059* (2013.01); *A61B 1/041* (2013.01); *A61B 5/7232* (2013.01)
USPC .......................................... 600/109; 600/118

(58) Field of Classification Search
USPC ...................................... 600/109, 118; 348/65
See application file for complete search history.

(56) References Cited

U.S. PATENT DOCUMENTS

| | | | | |
|---|---|---|---|---|
| 4,633,304 | A | * | 12/1986 | Nagasaki ......................... 348/69 |
| 5,604,531 | A | * | 2/1997 | Iddan et al. ...................... 348/76 |
| 6,612,981 | B2 | | 9/2003 | Onishi et al. |
| 6,840,901 | B2 | | 1/2005 | Onishi et al. |
| 6,853,310 | B2 | * | 2/2005 | Brinsfield ................. 340/870.41 |
| 6,902,529 | B2 | | 6/2005 | Onishi et al. |
| 6,904,308 | B2 | * | 6/2005 | Frisch et al. ................... 600/424 |

(Continued)

FOREIGN PATENT DOCUMENTS

| | | |
|---|---|---|
| JP | 07-289504 | 11/1995 |
| JP | 2001-353124 | 12/2001 |

(Continued)

OTHER PUBLICATIONS

Extended Supplementary European Search Report dated May 23, 2012 issued in counterpart European Patent Application No. 06835090.9.

(Continued)

*Primary Examiner* — Matthew J Kasztejna

(74) *Attorney, Agent, or Firm* — Scully, Scott, Murphy & Presser, P.C.

(57) ABSTRACT

A viewer includes a display unit. The display unit has a first display area for displaying an in-vivo image obtained by a first capsule endoscope received from a first receiver, and second display areas for displaying in-vivo images obtained by second capsule endoscopes received from second receivers. The viewer displays the in-vivo images in the first and second display areas, respectively.

5 Claims, 10 Drawing Sheets

(56) References Cited

U.S. PATENT DOCUMENTS

| | | | |
|---|---|---|---|
| 7,109,933 B2 * | 9/2006 | Ito et al. | 343/718 |
| 7,354,397 B2 * | 4/2008 | Fujita et al. | 600/109 |
| 7,505,062 B2 * | 3/2009 | Davidson et al. | 348/77 |
| 7,650,180 B2 * | 1/2010 | Glukhovsky et al. | 600/476 |
| 2002/0173718 A1 * | 11/2002 | Frisch et al. | 600/424 |
| 2003/0023150 A1 | 1/2003 | Yokoi et al. | |
| 2003/0097042 A1 | 5/2003 | Eino | |
| 2003/0151661 A1 | 8/2003 | Davidson et al. | |
| 2004/0082834 A1 * | 4/2004 | Onishi et al. | 600/118 |
| 2005/0043634 A1 * | 2/2005 | Yokoi et al. | 600/476 |
| 2005/0165272 A1 * | 7/2005 | Okada et al. | 600/114 |

FOREIGN PATENT DOCUMENTS

| | | |
|---|---|---|
| JP | 2003-19111 | 1/2003 |
| JP | 2003-093339 A | 4/2003 |
| JP | 2003-135371 | 5/2003 |
| JP | 2004-024340 A | 1/2004 |
| JP | 2004-113780 A | 4/2004 |
| JP | 2004-121613 A | 4/2004 |
| JP | 2004-275321 A | 10/2004 |
| JP | 2005-021392 A | 1/2005 |
| JP | 2006-305369 A | 11/2006 |
| JP | 2007-130227 A | 5/2007 |
| JP | 2008-307122 A | 12/2008 |

OTHER PUBLICATIONS

Decision of a Patent Grant dated Sep. 4, 2012 issued in counterpart Japanese Patent Application No. 2005-372670.

* cited by examiner

IN-VIVO IMAGE DISPLAY APPARATUS AND RECEIVING SYSTEM

CROSS-REFERENCE TO RELATED APPLICATIONS

This application is a continuation of PCT international application Ser. No. PCT/JP2006/325529 filed Dec. 21, 2006 which designates the United States, incorporated herein by reference, and which claims the benefit of priority from Japanese Patent Application No. 2005-372670, filed Dec. 26, 2005, incorporated herein by reference.

BACKGROUND OF THE INVENTION

1. Field of the Invention

The present invention relates to an in-vivo image display apparatus and a receiving system for receiving image data acquired by a body-insertable apparatus and displaying the image data.

2. Description of the Related Art

In recent years, in the field of body-insertable apparatuses such as endoscopes, there have been proposed capsule endoscopes capable of imaging function and radio communication function. During an observation period after such a capsule endoscope is swallowed by a subject for observation (examination) until the endoscope is naturally excreted from his/her body (human body), the capsule endoscope travels inside the organs (in the body cavity), such as esophagus, stomach and small intestine, along with their peristaltic motion. While traveling, the capsule endoscope successively captures images at a predetermined rate with the imaging function.

During the observation period in which the capsule endoscope travels inside the organs, image data captured by the capsule endoscope in the body cavity are successively transmitted via radio to the outside of the subject's body with the radio communication function, and stored in a memory of an external receiver. By carrying a receiver having the radio communication function and memory function, the subject is allowed to act freely even during the observation period after swallowing the capsule endoscope until excreting it. For example, Japanese Patent Application Laid-open No. 2003-19111 discloses a conventional technology related to such a receiving system.

To receive image data from the capsule endoscope, a general receiver includes a plurality of antennas. The antennas are set in places outside the subject's body to receive image signals transmitted from the capsule endoscope. The receiver switches the antennas from one to another while selecting one of them with high signal strength to receive the image signals from the selected one. In the conventional technology, a receiver switches a plurality of antennas set outside a subject's body and locates a capsule endoscope, i.e., an image signal source, inside the subject's body based on the electric field strength of a signal received by each antenna.

After completion of the operation of the capsule endoscope to capture images, generally, image data stored in the memory of the receiver is transferred to a workstation or the like and the images are viewed afterward. However, there has been an increasing demand from doctors for real-time viewing of images of, for example, areas of concern as well as areas such as the esophagus and stomach through which a capsule endoscope passes in a short time and thus which can be diagnosed immediately. To meet the demand, a system has been proposed that is provided with a simple in-vivo image display apparatus capable of real-time image display based on radio signals received from a capsule endoscope.

One of the simplest conventional in-vivo image display apparatuses is configured to be electrically connectable to a receiver, and includes a small display unit and a signal processor. With this configuration, upon receipt of a signal via the receiver, the signal processor performs predetermined processing on the signal and, based on the signal, the display unit displays an image captured by a capsule endoscope.

Having checked the position of a swallowed capsule endoscope and determined that it has reached a target organ of a subject, a doctor or the like observes the organ, and sometimes allows the subject to go out around the hospital after the observation. In such a case, it is required to locate the present position of the capsule endoscope. Generally, a doctor can recognize the intra-subject position of a capsule endoscope by checking an image received by an in-vivo image display apparatus. Besides, for example, when capsule endoscopy is performed in a plurality of patients at the same time, a doctor is required to recognize the position of each capsule endoscope.

SUMMARY OF THE INVENTION

An in-vivo image display apparatus according to an aspect of the present invention includes an image display unit, the image display unit having a first display area for displaying image data obtained inside a subject by a first body-insertable apparatus, and a second display area for displaying image data obtained inside a subject by a second body-insertable apparatus.

A receiving system according to another aspect of the present invention includes a plurality of radio transceivers that receive and transmit image data obtained inside subjects by a plurality of body-insertable apparatuses, and in-vivo image display apparatus. The radio transceivers include a first radio transceiver and a second radio transceiver. The in-vivo image display apparatus includes an image display unit having a first display area for displaying image data received from the first radio transceiver, and a second display area for displaying image data received from the second radio transceiver.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Exemplary embodiments of the present invention are explained in detail below with reference to the accompanying drawings.

Figure 1:
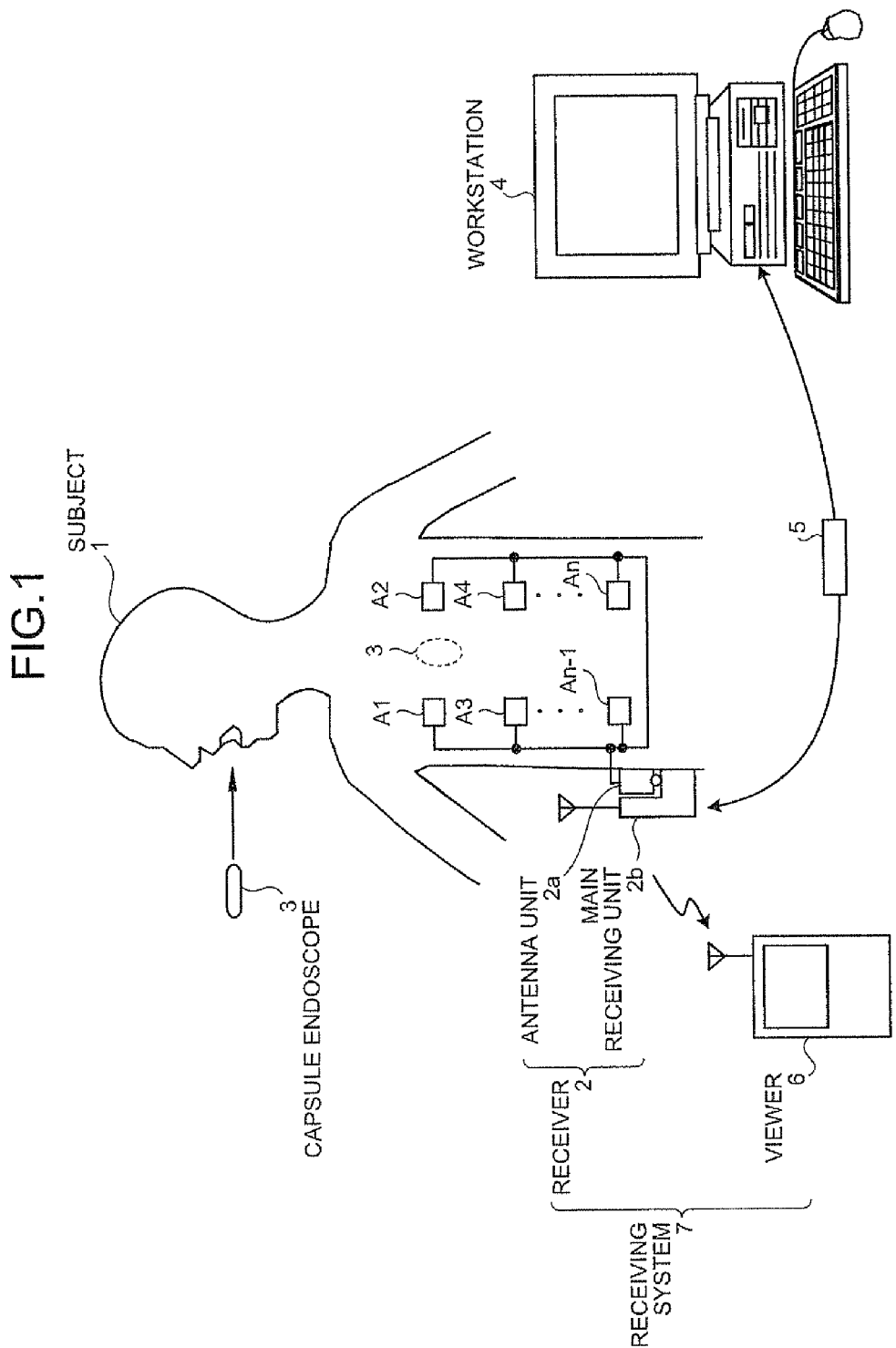
FIG. 1 is a schematic diagram of a radio in-vivo information acquiring system according to a first embodiment of the present invention.

FIG. 1 is a schematic diagram of a radio in-vivo information acquiring system according to a first embodiment of the present invention. The radio in-vivo information acquiring system includes a capsule endoscope 3 as a body-insertable apparatus, and a receiving system 7 that processes radio signals received from the capsule endoscope 3 inside a subject 1. The capsule endoscope 3 captures, when introduced into the subject 1, in-vivo images (body cavity images), and transmits data such as image signals to the receiving system 7.

The capsule endoscope 3 is introduced into the subject 1 through his/her mouth. The capsule endoscope 3 has a function of transmitting body cavity image data acquired with, for example, a built-in image-capturing mechanism via radio to the outside of the subject 1. A receiver 2 includes an antenna unit 2a and a main receiving unit 2b. The antenna unit 2a includes a plurality of receiving antennas A1 to An that are fixedly attached to the outer body surface of the subject 1 in appropriate places separated from one another. The main receiving unit 2b processes radio signals received via the receiving antennas A1 to An and the like. These units are detachably connected to each other via a connector or the like. The respective receiving antennas A1 to An can be attached to, for example, a jacket that the subject 1 can wear so that the subject 1 is fitted with the receiving antennas A1 to An by wearing the jacket. In this case, the receiving antennas A1 to An can be detachable from the jacket.

The radio in-vivo information acquiring system further includes a workstation 4, and a portable recording medium 5. The workstation 4 displays body cavity images based on image signals received by the receiver 2. The portable recording medium 5 serves as a storage unit for exchanging data between the receiver 2 and the workstation 4.

The workstation 4 functions as a display device that displays body cavity images captured by the capsule endoscope 3 and the like, and displays images based on data obtained from the portable recording medium 5 and the like. More specifically, the workstation 4 directly displays an image on a cathode ray tube (CRT) display, a liquid crystal display (LCD), or the like. The workstation 4 is not thus limited, and can be configured to output an image through another medium such as a printer.

The portable recording medium 5 can be, for example, a CompactFlash® memory, and is connectable to and disconnectable from the main receiving unit 2b and the workstation 4. The portable recording medium 5 is configured such that, when connected to any one of the main receiving unit 2b and the workstation 4, it outputs or receives information. In the first embodiment, for example, the portable recording medium 5 is connected to the workstation 4 before a test to record identification information such as a test ID. The portable recording medium 5 is connected to the main receiving unit 2b immediately before the test so that the identification information recorded thereon is read and registered in the main receiving unit 2b. While the capsule endoscope 3 travels in the body cavity of the subject 1, the portable recording medium 5 is connected to the main receiving unit 2b attached to the subject 1, and records data received from the capsule endoscope 3. After the capsule endoscope 3 is excreted from the subject 1, that is, after completion of image capturing inside the subject 1, the portable recording medium 5 is ejected from the main receiving unit 2b and connected to the workstation 4. Various data, such as image data, recorded on the portable recording medium 5 is read by the workstation 4. Such a data exchange between the main receiving unit 2b and the workstation 4 via the portable recording medium 5, for example, allows the subject 1 to act freely during capture of images in the body cavity as well as reducing the time taken to deriver data to the workstation 4. The main receiving unit 2b can be, for example, a built-in recording device such as a hard disk, and connected via wire or wireless connection to the workstation 4 for data exchange therebetween.

Figure 2:
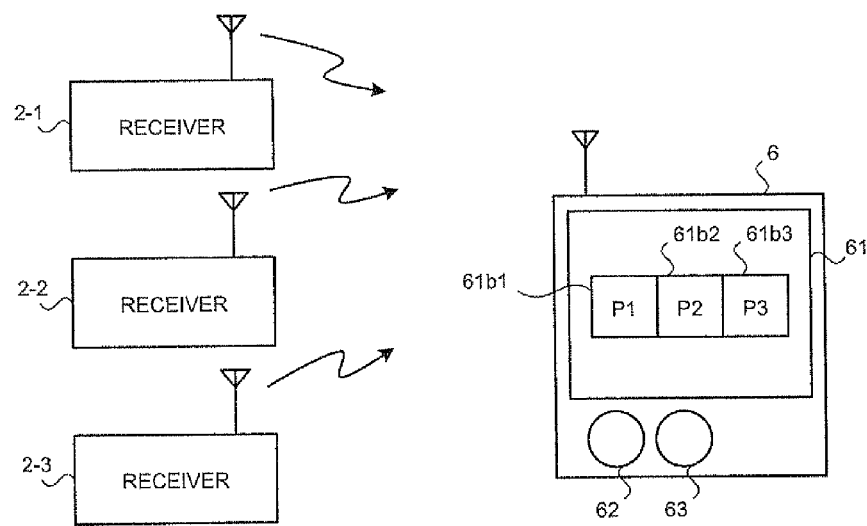
FIG. 2 is a schematic diagram of the receiving system shown in FIG. 1.
Figure 3:
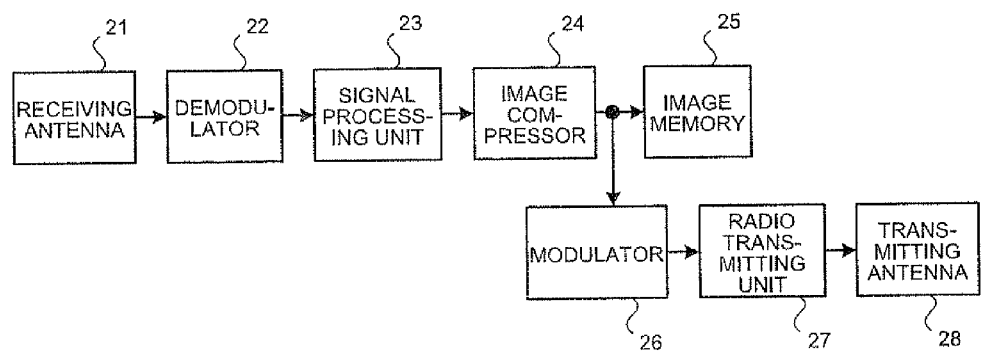
FIG. 3 is a functional block diagram of a receiver shown in FIG. 2.

FIG. 2 is a schematic diagram of the receiving system 7. The receiving system 7 includes a plurality of receivers 2 (in the first embodiment, for example, three receivers 2-1 to 2-3) that is used as being carried by the subject 1 and receives radio signals, and a viewer 6 that is connected via radio to the receivers 2-1 to 2-3. The viewer 6 serves as an in-vivo image display apparatus that displays images captured by the capsule endoscope 3 based on radio signals output from the respective receivers 2-1 to 2-3. The receivers 2-1 to 2-3 are of the same configuration as shown in FIG. 3. For example, in mass health screening, the receivers 2-1 to 2-3 each receive a radio signal from the capsule endoscope 3 introduced into a different subject and process it. More specifically, the receivers 2-1 to 2-3 each include a receiving antenna 21, a demodulator 22, a signal processing unit 23, an image compressor 24, and an image memory 25. The receivers 2-1 to 2-3 receive a radio signal from the capsule endoscope 3 via one of a plurality of receiving antennas (the receiving antennas A1 to An), for example, the receiving antenna 21 with the highest received signal strength. The demodulator 22 demodulates the radio signal. The signal processing unit 23 performs signal processing (including, in addition to general image processing, color enhancement processing and white balance processing) on an image signal obtained by demodulating the radio signal to obtain image data. Thereafter, the image compressor 24 compresses the image data, and the compressed image data is stored in the image memory 25. Apart from the configuration of an ordinary receiver of image data as described above, the receivers 2-1 to 2-3 of the first embodiment each further include a modulator 26, a radio transmitting unit 27, and a transmitting antenna 28. The modulator 26 modulates image data compressed by the image compressor 24. The radio transmitting unit 27 transmits the modulated image data as a radio signal through the transmitting antenna 28. Thus, the subject 1 is required to carry only one receiver.

The viewer 6 receives radio signals transmitted from the receivers 2-1 to 2-3, and, based on the radio signals, sequentially displays body cavity images captured by the capsule endoscope 3. The viewer 6 is portable, and of a size that allows the operator to carry it by hand. The viewer 6 has functions of directly receiving radio signals from the receivers 2-1 to 2-3 as well as displaying images based on the radio signals. To implement the functions, the viewer 6 includes a rod-shaped receiving antenna 31 and an image display unit 61. The receiving antenna 31 is formed integrally with the viewer 6. The image display unit 61 includes a small LCD. The output frequencies of the receivers 2-1 to 2-3 can be set to different values so that the viewer 6 can distinguish them based on the output frequencies. Alternatively, the viewer 6 can be connected for signal transmission/reception to the receivers 2-1 to 2-3 via, for example, a wireless LAN, and each signal from the receivers 2-1 to 2-3 can include a parameter to allow the viewer 6 to distinguish them. The viewer 6 is provided with an image selector button 62 for selecting an image and a switch 63 for switching display modes on the viewer 6.

Figure 4:
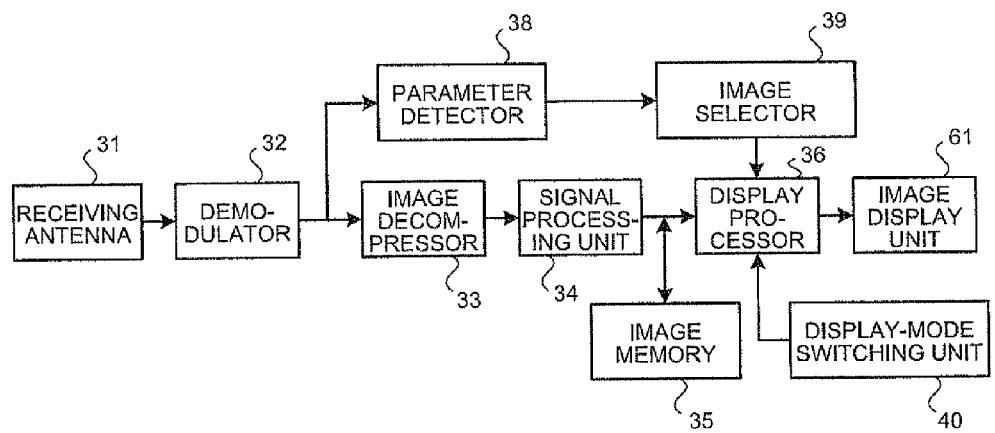
FIG. 4 is a functional block diagram of a viewer shown in FIG. 2.

FIG. 4 is a functional block diagram of the viewer 6 according to the first embodiment. As shown in FIG. 4, the viewer 6 includes the receiving antenna 31, a demodulator 32, an image decompressor 33, a signal processing unit 34, an image memory 35, a display processor 36, and the image display unit 61. The demodulator 32 demodulates a radio signal received from the receivers 2-1 to 2-3 via the receiving antenna 31. The image decompressor 33 decompresses an image signal obtained by demodulating the radio signal. The signal processing unit 34 performs signal processing on the decompressed image signal to obtain image data, and stores the image data in the image memory 35. The image memory 35 sequentially stores therein image data in association with a parameter. The display processor 36 performs display processing on the image data stored in the image memory 35. The image display unit 61 displays the image data having been subjected to the display processing by the display processor 36. The viewer 6 further includes a parameter detector 38, an image selector 39, and a display-mode switching unit 40. The parameter detector 38 detects a predetermined parameter included in a radio signal received from each of the receivers 2-1 to 2-3 and demodulated by the demodulator 32. The image selector 39 issues an instruction to select an image based on the parameter. The display-mode switching unit 40 switches display modes of image data received from the receivers 2-1 to 2-3. With this configuration, the viewer 6 enables multi-image display, i.e., multi-image mode, for displaying a plurality of images, and real-time display, i.e., single image mode, for sequentially displaying an image.

The parameter detector 38 detects, from a radio signal demodulated by the demodulator 32, a parameter such as an examination ID or a patient ID that uniquely identifies each patient. The image selector 39 includes the image selector button 62 for selecting a predetermined image. From parameters detected by the parameter detector 38, the image selector 39 selects a parameter corresponding to an image selected by depression of the image selector button 62.

Figure 5:
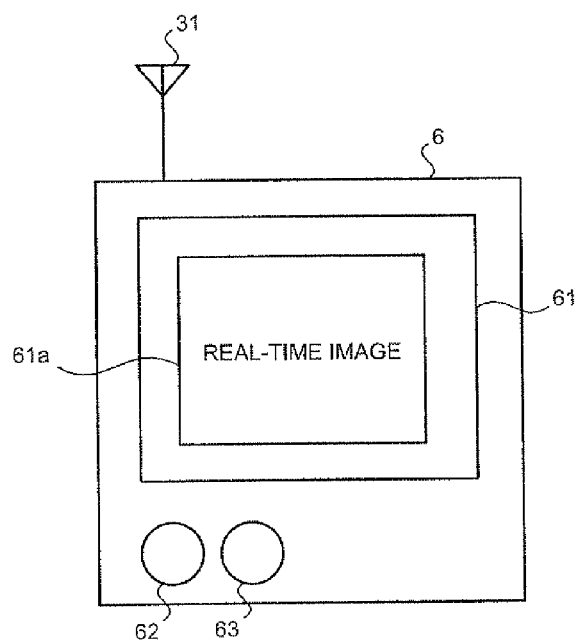
FIG. 5 is a schematic external view of the viewer in single image mode.

The display processor 36 switches the display mode to the real-time display in response to depression of the switch 63. Based on the parameter selected by the image selector 39, the display processor 36 provides real-time image display through the image display unit 61. In the initial state, the image display unit 61 displays images in the multi-image mode under the control of the display processor 36. That is, as shown in FIG. 2, the image display unit 61 displays image data P1 received from the receiver 2-1 in a first display area 61b1, and displays image data P2 and P3 received from the receivers 2-2 and 2-3 in second display areas 61b2 and 61b3, respectively. When an image is selected, the image display unit 61 displays, in real time, the selected image. That is, as shown in FIG. 5, the image display unit 61 sequentially displays the selected image in enlarged form in an image display area 61a as a real-time display section. Incidentally, the image display unit 61 can be a touch panel, so that an image can be selected by touching an image displayed on the touch panel instead of depressing the image selector button 62.

Figure 6:
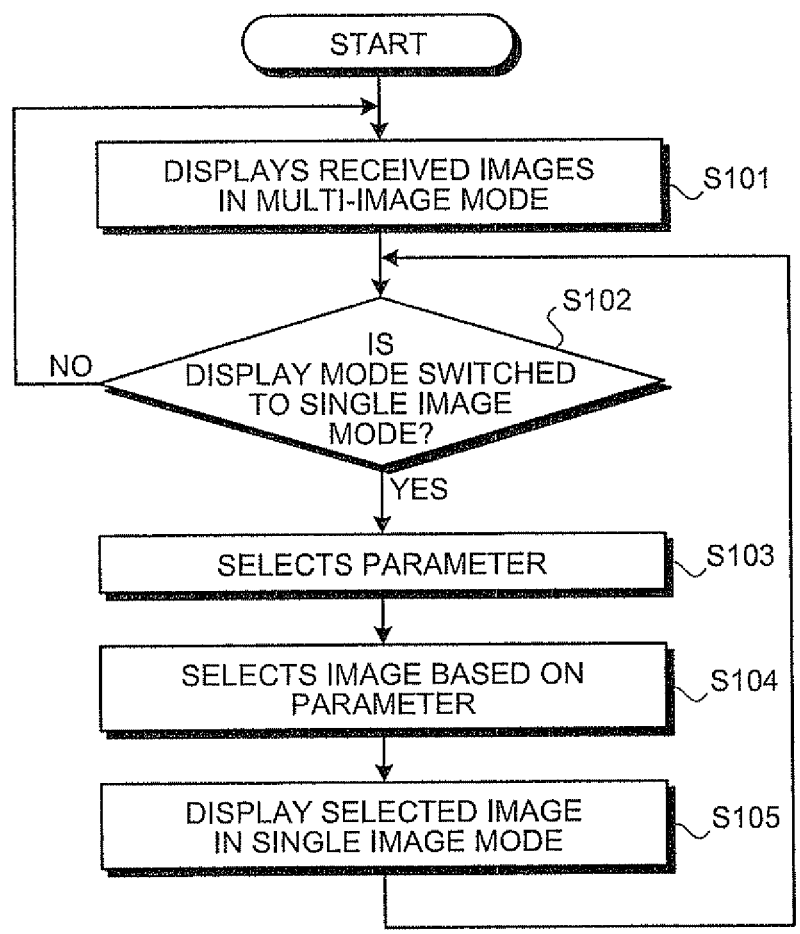
FIG. 6 is a flowchart of the operation of the viewer for image display.

The operation of the viewer 6 for image display is explained below with reference to FIG. 6. A plurality of images received via the receiving antenna 31 from the receivers 2-1 to 2-3 are stored in the image memory 35. The display processor 36 displays the images stored in the image memory 35 in the multi-image mode (step S101). At this time, as shown in FIG. 2, the display processor 36 sequentially displays images captured during a predetermined time period and received from the receivers 2-1 to 2-3 as, for example, still images in the respective display areas 61b1 to 61b3 of the image display unit 61. The display processor 36 stores in advance parameters received from the receivers 2-1 to 2-3 in association with the receivers 2-1 to 2-3, respectively. Thus, based on parameters detected by the parameter detector 38, images received from the receivers 2-1 to 2-3 can be associated with the respective receivers 2-1 to 2-3.

When the switch 63 of the display-mode switching unit 40 is depressed and an image is selected from the images received from the receivers 2-1 to 2-3 with the image selector button 62, the display mode is switched to the single image mode (Yes at step S102). Then, from parameters detected by the parameter detector 38, the image selector 39 selects a parameter corresponding to the selected image (step S103).

When a parameter is selected by the image selector 39, the display processor 36 selects a corresponding image from images stored in the image memory 35 based on the parameter (step S104). The display processor 36 displays the selected image in real time in the image display area 61a of the image display unit 61 in the single image mode (step S105). When the switch 63 of the display-mode switching unit 40 is depressed again, the display processor 36 determines that an instruction is provided to switch the display mode to the multi-image mode (No at step S102), and displays received images in the multi-image mode on the image display unit 61 (step S101). While, in the first embodiment, the viewer 6 receives a radio signal indirectly from a capsule endoscope via a receiver carried by a patient, the viewer 6 can receive a radio signal directly from a capsule endoscope without the interposition of a receiver.

As described above, according to the first embodiment, the image display unit 61 is provided with the first display area 61b1 for displaying image data obtained by a first capsule endoscope and received from the receiver 2-1, and the second display areas 61b2 and 61b3 for displaying image data obtained by second capsule endoscopes and received from the receivers 2-2 and 2-3. The viewer 6 receives a plurality of body cavity images of a plurality of subjects transmitted from a plurality of capsule endoscopes via the receivers 2-1 to 2-3. Thus, the body cavity images can be observed on one viewer. Moreover, it is possible to locate and determine the intra-subject position of a capsule endoscope.

The image display unit 61 is further provided with the image display area 61a for sequentially displaying image data directly received from the receivers 2-1 to 2-3, and the display mode is switched from one to another as required. Therefore, for example, by switching the multi-image display to the real-time display to display body cavity images of a specific patient in enlarged form, the body cavity images can be observed in real time. This improves observation accuracy, and thus improves the usability of the viewer 6.

Figure 7:
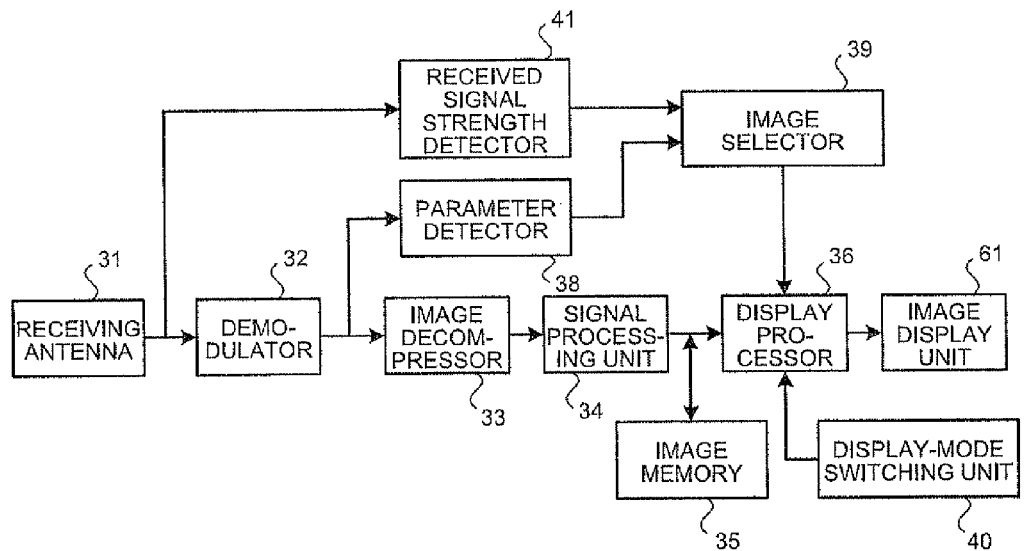
FIG. 7 is a functional block diagram of a viewer according to a second embodiment.

FIG. 7 is a functional block diagram of the viewer 6 according to a second embodiment of the present invention. As shown in FIG. 7, the viewer 6 of the second embodiment is different from that of the first embodiment in that it further includes a received signal strength detector 41. The received signal strength detector 41 detects the strength of radio signals received via the receiving antenna 31. An image corresponding to a received radio signal with the highest signal strength is selected to be displayed in real time. In other words, the received signal strength detector 41 detects the strength of a radio signal received via the receiving antenna 31 from each receiver. The parameter detector 38 detects a parameter from the radio signal. That is, the received signal strength and the parameter corresponds to the same radio signal received via the receiving antenna 31. In the single image mode, the image selector 39 selects a parameter of a radio signal corresponding to the highest signal strength among received signal strengths detected by the received signal strength detector 41. The display processor 36 displays, in the multi-image mode, a plurality of images, which have been received via the receiving antenna 31 from the receivers 2-1 to 2-3 and stored in the image memory 35, on the image display unit 61. On the other hand, in the single image mode, the display processor 36 displays, in real time, an image corresponding to the highest signal strength selected from among images received from the receivers 2-1 to 2-3 on the image display unit 61.

For example, when brought close to a specific patient whose body cavity images are desired to be displayed in real time, the viewer 6 can receive radio signals with the highest signal strength from a receiver carried by the patient (or radio signals from the capsule endoscope 3 inside the subject 1). The display processor 36 displays, in teal time, an image based on a parameter selected by the image selector 39 on the image display unit 61 in the single image mode. Incidentally, in the second embodiment, the image selector button 62 can also be used as in the first embodiment, so that an image can be selected by the image selector button 62 as well as by detection of received signal strength.

As described above, according to the second embodiment, in the single image mode, a parameter can be selected by only bringing the viewer 6 close to a specific patient, and, based on the parameter, an image can be displayed, in real time, in enlarged form in the image display area 61a of the image display unit 61. This further improves the usability of the viewer 6.

Figure 8:
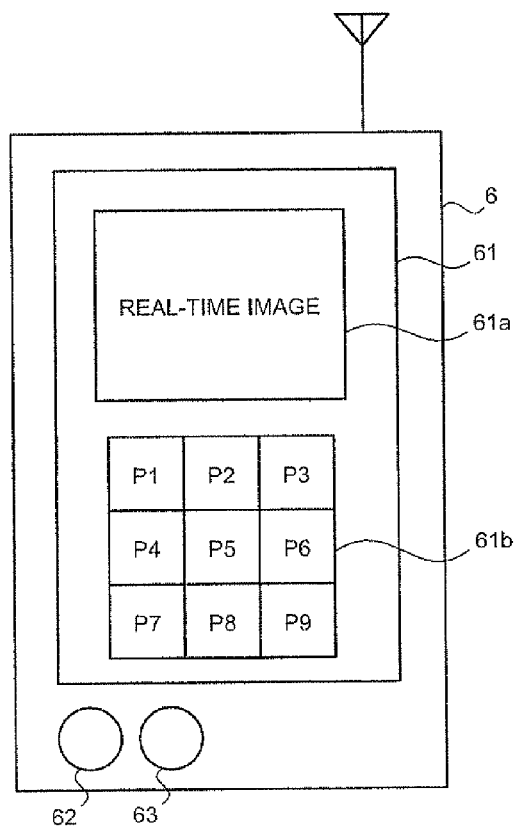
FIG. 8 is a schematic external view of a viewer according to a third embodiment.

FIG. 8 is a schematic external view of the viewer 6 according to a third embodiment of the present invention. In the first embodiment described above, the display mode of the image display unit 61 is switched between the multi-image display and the real-time display in response to depression of the switch 63. Differently from the first embodiment, in the third embodiment, as shown in FIG. 8, the multi-image mode and the single image mode are active at the same time. More specifically, image data received from, for example, nine receivers 2-1 to 2-9 are displayed in a display area group 61b including a plurality of display areas in the multi-image mode. At the same time, image data selected with the image selector button 62 from the image data received from the receivers 2-1 to 2-9 is displayed in the image display area 61a in real time.

Figure 9:
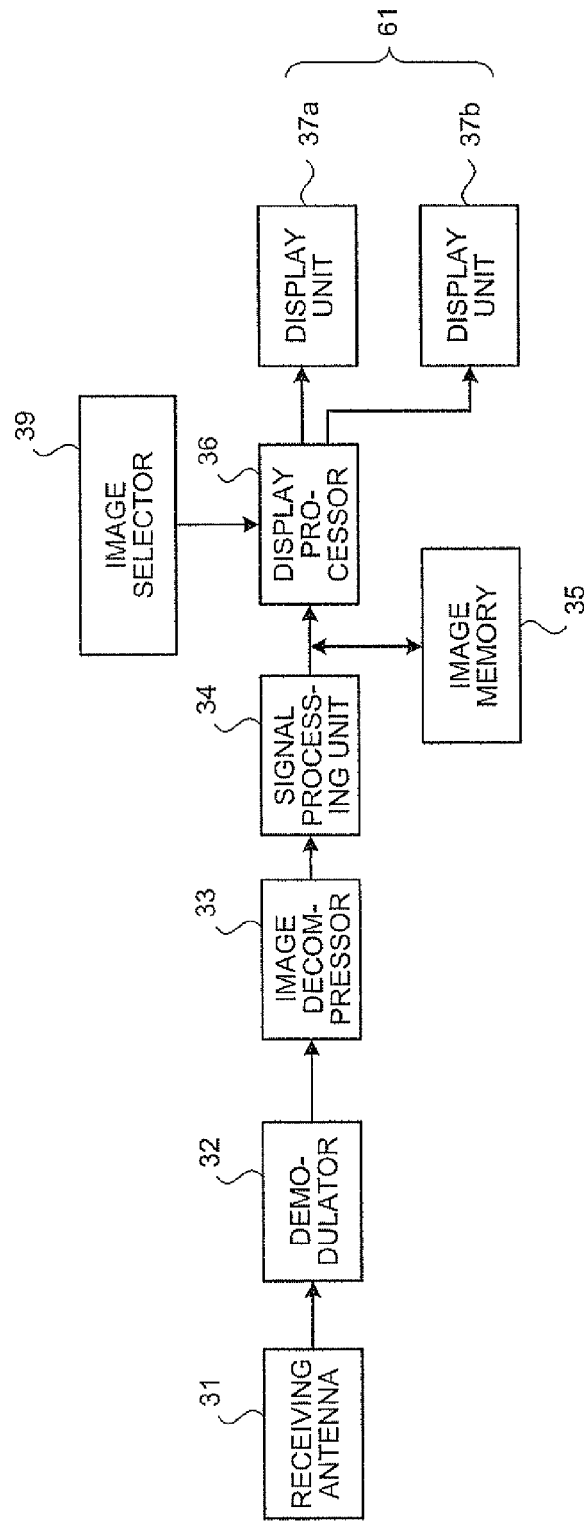
FIG. 9 is a functional block diagram of the viewer according to the third embodiment.

FIG. 9 is a functional block diagram of the viewer 6 according to the third embodiment. As shown in FIG. 9, in the viewer 6 of the third embodiment, the image display unit 61 includes two display units 37a and 37b each formed of LCD, so that the display processor 36 can perform the multi-image display and the real-time display at the same time. More specifically, the display processor 36 sequentially reads an image specified by the image selector 39 from the image memory 35, and displays, in real time, the image in enlarged form, for example, in the display unit 37a. The display processor 36 sequentially reads a plurality of images P1 to P9 received form the receivers 2-1 to 2-9 from the image memory 35, and displays them in the display unit 37b.

According to the third embodiment, the multi-image display, in which images from a plurality of capsule endoscopes are displayed, can be performed along with the real-time display, in which a selected image is displayed in real time. Thus, it is possible to locate and determine the intra-subject position of each capsule endoscope at the same time as real-time observation of a specific image. As a result, the usability of the viewer 6 can be further improved.

While, in the third embodiment, the multi-image display and the real-time display are performed by two display units each formed of LCD, the present invention is not thus limited. For example, a display unit formed of a single LCD can be used for the same effect by dividing its display area into two, one for the real-time display with a single image, the other for the multi-image display.

Figure 10:
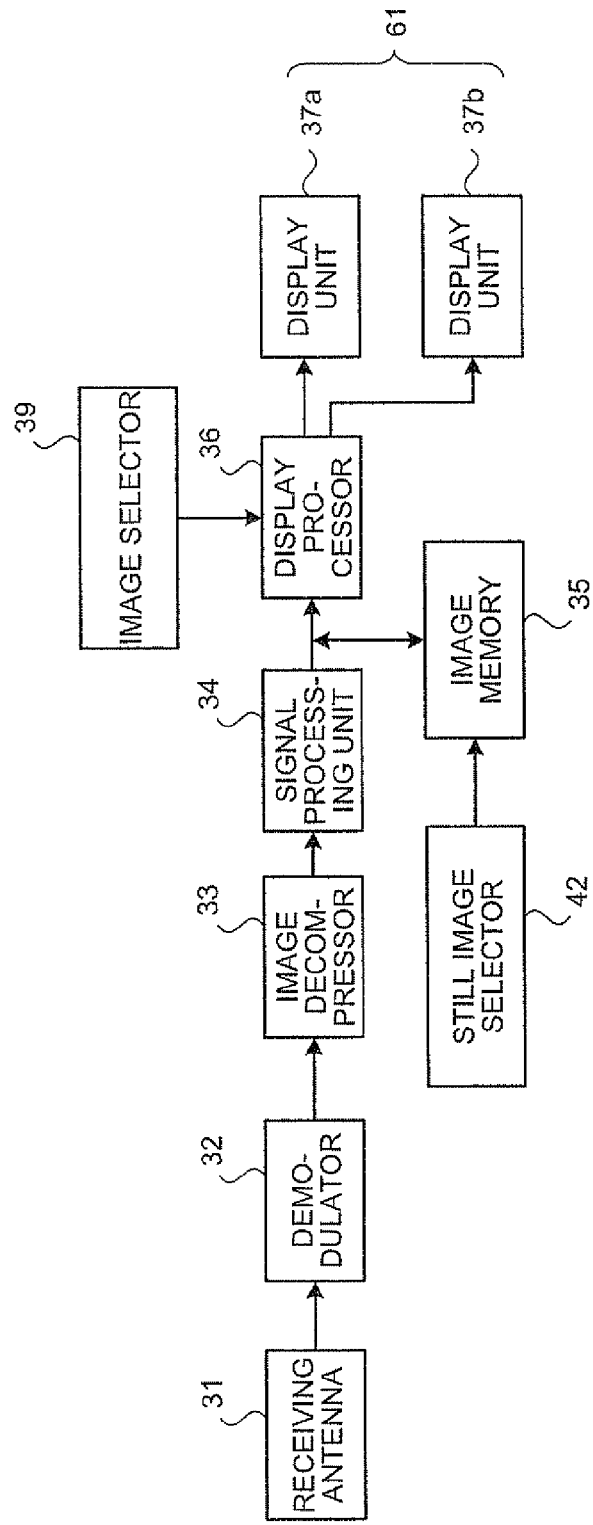
FIG. 10 is a functional block diagram of a viewer according to a fourth embodiment.

FIG. 10 is a functional block diagram of the viewer 6 according to a fourth embodiment of the present invention. As shown in FIG. 10, the viewer 6 of the fourth embodiment is different from that of the third embodiment in the presence of a still image selector 42. The still image selector selects a still image from received images, and still-image display is switched to the real-time display and vice versa. The still image selector 42 includes, for example, a button (not shown) for selecting a still image, and, in response to depression of the button, issues a trigger indicating that an image has been selected. The image memory 35 has an image storage area for storing images received from the receivers 2-1 to 2-9 and a still-image storage area for storing still images. Upon issuance of such a trigger, the image memory 35 stores a corresponding image not in the image storage area but in the still-image storage area. The display processor 36 separately reads a still image and images received from the receivers from the still-image storage area and the image storage area, respectively. The display processor 36 then displays the still image selected by the still image selector 42 through, for example, the display unit 37a, and displays the respective received images in the display unit 37b.

Incidentally, in the fourth embodiment, the display unit 37a can be set to display a specific image selected by the still image selector 42 from predetermined images to be displayed in real time, while the display unit 37b can be set to sequentially perform the multi-image display. The display unit 37b can also be set to display all images to be displayed in multi-image mode selected by the still image selector 42 as still images, while the display unit 37a can be set to perform the real-time display. Further, the display unit 37a can be set to display a specific image selected from images being displayed in multi-image mode as a still image, while the display unit 37b can be set to sequentially perform the multi-image display.

As described above, according to the fourth embodiment, a specific image can be selected by the still image selector 42 from images displayed in real time and in multi-image display, so that the display processor 36 can display a still image. As a result, the usability of the viewer 6 can be further improved.

Figure 11:
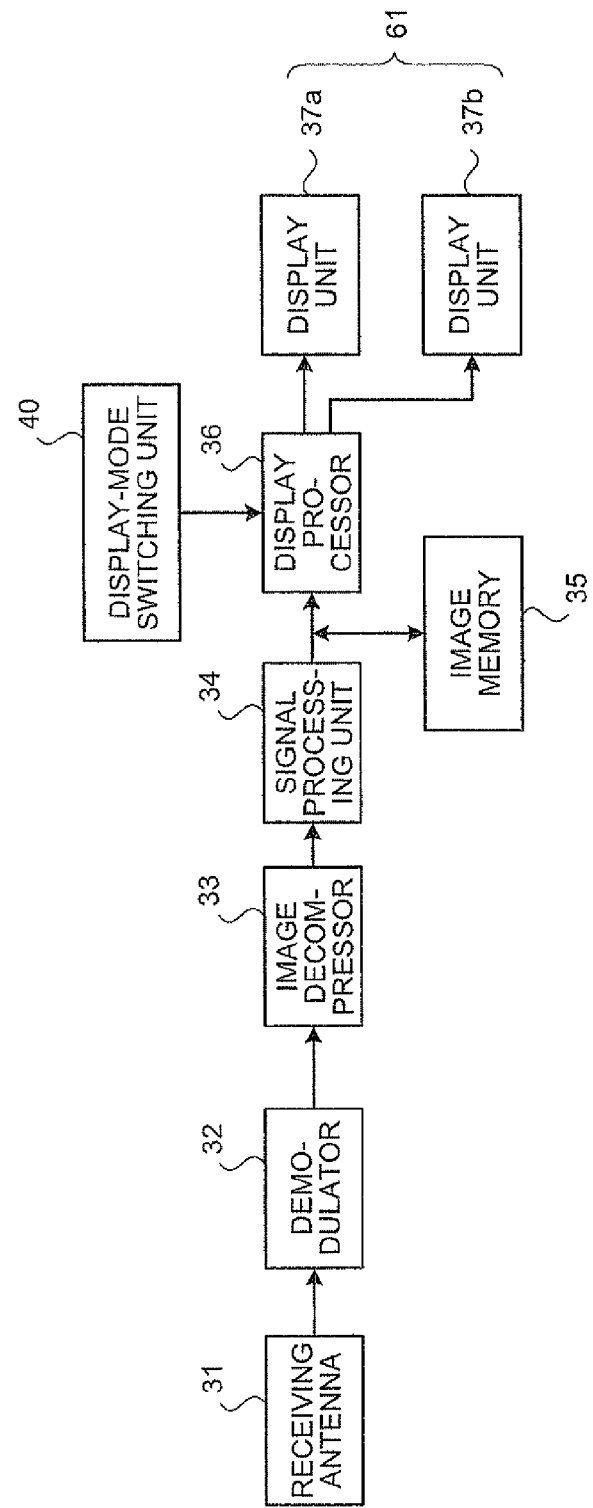
FIG. 11 is a functional block diagram of a viewer according to a fifth embodiment.

FIG. 11 is a functional block diagram of the viewer 6 according to a fifth embodiment of the present invention. As shown in FIG. 11, the viewer 6 of the fifth embodiment is different from that of the third embodiment in the presence of the display-mode switching unit 40. The display-mode switching unit 40 switches the display mode to zoom-in/out an image, and displays a zoom-in image or a zoom-out image by the display unit 37b according to an instruction. The display-mode switching unit 40 includes, for example, a zoom in/out switch button (not shown). In response to depression of the zoom in/out switch button as an instruction to zoom in a predetermined image displayed in real time by the display unit 37a, the display-mode switching unit 40 zooms in the predetermined image so that the zoom-in image is displayed by the display unit 37b. On the other hand, in response to depression of the zoom in/out switch button as an instruction to zoom out an image displayed by the display unit 37a, the display-mode switching unit 40 zooms out the image so that the zoom-out image is displayed by the display unit 37b. The image displayed by the display unit 37b can be a still image, or the same real-time image as that displayed in real time by the display unit 37a in either zoomed in/out state.

As described above, according to the fifth embodiment, in response to an instruction from the display-mode switching unit 40 to zoom in/out an image displayed in real time by the display unit 37a, the display processor 36 can display a zoom-in/out image. As a result, the usability of the viewer 6 can be further improved.

Incidentally, the viewer 6 of the fifth embodiment can further be provided with the image selector 39 shown in FIG. 9. If the viewer 6 is set such that, in the initial state, the display unit 37a performs the real-time display with a single image while the display unit 37b performs the multi-image display, and an instruction can be issued from the display-mode switching unit 40 to zoom in/out an image selected by the image selector 39, the usability of the viewer 6 can be further improved.

Figure 12:
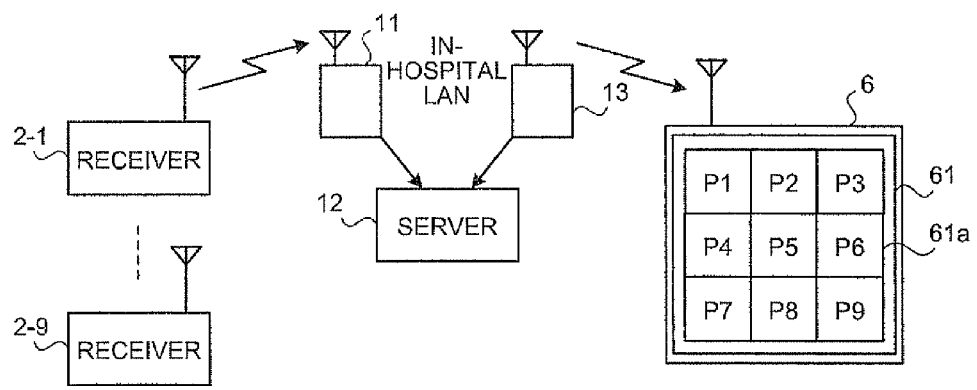
FIG. 12 is a schematic diagram of another example of a receiving system.

FIG. 12 is a schematic diagram of another example of a receiving system. As shown in FIG. 12, the receiving system of the sixth embodiment includes, for example, the nine receivers 2-1 to 2-9, a receiver 11, a server 12, a transmitter 13, and the viewer 6. The receiver 11 is connected via radio to the receivers 2-1 to 2-9, and receives radio signals output therefrom. Upon receipt of the radio signals via the receiver 11, the server 12 performs predetermined signal processing on the radio signals. The transmitter 13 transmits the radio signals having been subjected to the signal processing in the server 12. Based on the radio signals received from the transmitter 13, the viewer 6 displays images captured by respective capsule endoscopes. In this case, the receiver 11, the server 12, and the transmitter 13 constitute in-house LAN such as in-hospital LAN. The receivers 2-1 to 2-9 are of the same configuration as those shown in FIG. 2, and the receiver 11 and the transmitter 13 are commonly used devices for relaying signals. Therefore, a detailed explanation thereof is not deemed necessary herein.

Figure 13:
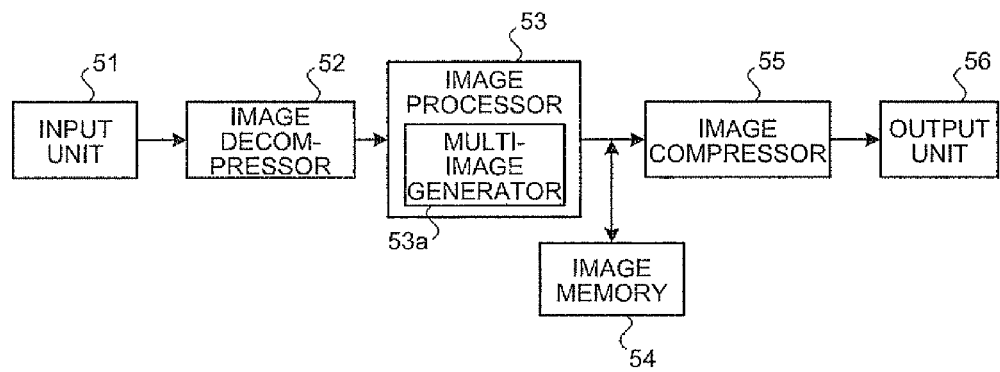
FIG. 13 is a functional block diagram of a server according to a sixth embodiment.

As shown in FIG. 13, the server 12 includes an input unit 51, an image decompressor 52, an image processor 53, an image memory 54, an image compressor 55, and an output unit 56. The input unit 51 receives an image signal obtained by demodulating a radio signal in the receiver 11. The image decompressor 52 decompresses the image signal, and the image processor 53 performs signal processing on the decompressed image signal. The image processor 53 performs general image processing, color enhancement processing, white balance processing, and the like, and includes a multi-image generator 53a. The multi-image generator 53a converts each image received from each of the receivers 2-1 to 2-9 into a single set of image data (hereinafter, "combined multi-image"), and stores the combined multi-image in the image memory 54. The image compressor 55 reads the combined multi-image from the image memory 54 to compress it. The output unit 56 outputs the combined multi-image compressed by the image compressor 55 to the transmitter 13. The transmitter 13 modulates the combined multi-image received from the server 12, and transmits it to the viewer 6.

Figure 14:
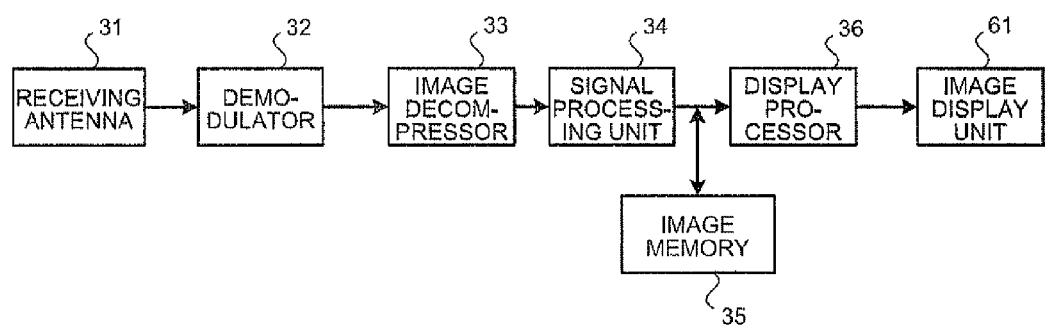
FIG. 14 is a functional block diagram of a viewer according to a sixth embodiment.

As shown in FIG. 14, in the viewer 6, the demodulator 32 demodulates a radio signal received via the receiving antenna 31. The image decompressor 33 decompresses an image signal obtained by demodulating the radio signal. The signal processing unit 34 performs signal processing on the decompressed image signal to obtain image data, and stores the image data in the image memory 35 as a combined multi-image for a single image display. The display processor 36 reads combined multi-images from the image memory 35, and performs display processing on the combined multi-images. Thus, the image display unit 61 displays the respective combined multi-images.

As described above, according to the sixth embodiment, in mass health screening, for example, image data are transmitted from a plurality of capsule endoscopes via the in-hospital LAN to the viewer 6, and displayed in multi-image display. Accordingly, body cavity images of a plurality of subjects transmitted from the capsule endoscopes can be observed on one viewer. Moreover, it is possible to locate and determine the intra-subject position of each capsule endoscope.

Furthermore, the server 12 receives image data transmitted from different capsule endoscopes, and converts the image data into a single set of image data. The server 12 then transmits the image data (combined multi-image) to the viewer 6 so that the image data can be displayed. Therefore, the memory capacity required of the viewer 6 can be substantially less than that of a viewer that separately receives image data from respective receivers and converts them into combined multi-image. As a result, the receiving system requires less cost.

Besides the configuration described in the first to sixth embodiments, for example, when it is determined that a capsule endoscope has reached a target organ of a subject for a test and an image is selected on a viewer, a notification can be transmitted to a corresponding receiver to notify the subject that he/she is allowed to go out of the hospital. With this, the subject can act freely even during the observation period before the endoscope is excreted from the subject's body.

Apart from a still image, a zoom-in/out image, and a multi-image display, an image that has been subjected to color enhancement and structure enhancement can be displayed in a different display on a viewer. That is, a plurality of images each having undergone different image processing can be displayed on the same viewer. This improves observation accuracy, and thus further improves the usability of the viewer 6.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An in-vivo image display system for displaying in-vivo images received from a plurality of body-insertable apparatuses respectively inserted in a plurality of subjects, the in-vivo image display system comprising:
  an in-vivo image display apparatus comprising a first display unit, the first display unit having:
    a first display area for displaying image data obtained inside a first subject by a first body-insertable apparatus, and a second display area for displaying image data obtained inside a second subject by a second body-insertable apparatus; and a first receiver carried by the first subject for receiving the image data obtained inside the first subject, and transmitting the image data to the in-vivo image display apparatus as a first radio signal; and a second receiver carried by the second subject for receiving the image data obtained inside the second subject, and transmitting the image data to the in-vivo image display apparatus as a second radio signal, wherein the in-vivo image display apparatus further comprises a received signal strength detector having a display mode for:

detecting a strength of the first radio signal received from the first receiver and a strength of the second radio signal received from the second receiver, determining that the strength of the first radio signal is stronger than the strength of the second radio signal, selecting the first receiver based on the determination that the strength of the first radio signal is stronger than the strength of the second radio signal, and displaying the image data obtained inside the first subject by the first body-insertable apparatus based on the selection of the first receiver.

2. The in-vivo image display system according to claim 1, wherein the first display unit displays image data of a still image, and wherein the in-vivo image display apparatus further comprises a second display unit that sequentially receives image data from any one of the first body-insertable apparatus and the second body-insertable apparatus directly or indirectly, and sequentially displays the image data in real time.

3. The in-vivo image display system according to claim 1, wherein the output frequency of the first radio signal and the output frequency of the second radio signal are set to different values.

4. The in-vivo image display system according to claim 1, wherein the first radio signal transmitted by the first receiver has a parameter for identifying the first receiver and the second radio signal transmitted by the second receiver has a parameter for identifying the second receiver.

5. The in-vivo image display system according to claim 1, further comprising an image selector for switching between displaying image data for one image and displaying image data for a plurality of images.

\* \* \* \* \*